United States Patent [19]

Schneider et al.

[11] Patent Number: 5,795,855
[45] Date of Patent: Aug. 18, 1998

[54] ENHANCEMENT OF LACCASE REACTIONS

[75] Inventors: Palle Schneider, Ballerup; Anders Hjelholt Pedersen, Lyngby, both of Denmark

[73] Assignee: Novo Nordisk A/S, Bagsvaerd

[21] Appl. No.: 569,101

[22] PCT Filed: May 31, 1994

[86] PCT No.: PCT/DK94/00210

§ 371 Date: Dec. 21, 1995

§ 102(e) Date: Dec. 21, 1995

[87] PCT Pub. No.: WO95/01426

PCT Pub. Date: Jan. 12, 1995

[30] Foreign Application Priority Data

Jun. 29, 1993 [DK] Denmark ................... 0773/93

[51] Int. Cl.$^6$ ............... C11D 3/386; C11D 3/26; C11D 3/393
[52] U.S. Cl. ............. 510/376; 510/302; 510/303; 510/305; 510/300; 510/312; 510/313; 510/367; 510/374; 8/101
[58] Field of Search ............... 510/302, 303, 510/305, 300, 312, 313, 367, 374, 376; 8/101

[56] References Cited

U.S. PATENT DOCUMENTS

| | | | |
|---|---|---|---|
| 4,634,551 | 1/1987 | Burns et al. | 252/102 |
| 5,360,569 | 11/1994 | Madison | 252/102 |
| 5,445,755 | 8/1995 | Convents et al. | 252/102 |
| 5,451,337 | 9/1995 | Liu et al. | 252/102 |

FOREIGN PATENT DOCUMENTS

WO 91/05839  5/1991  WIPO.
WO 92/20857  11/1992  WIPO.

*Primary Examiner*—Paul Lieberman
*Assistant Examiner*—Kery A. Fries
*Attorney, Agent, or Firm*—Steve T. Zelson, Esq.; Elias J. Lambiris, Esq.

[57] ABSTRACT

This invention relates to methods of oxidizing a substrate in the presence of a laccase or a laccase related enzyme and an enhancing agent. More specifically, the invention relates to a method of bleaching of dye in solutions, to a method of inhibiting the transfer of a textile dye from a dyed fabric to another fabric when said fabrics are washed together in a wash liquor, to a method of bleaching of lignin-containing material, in particular bleaching of pulp for paper production, to a method of treatment of waste water from pulp manufacturing, and to a method of enzymatic polymerization and/or modification of lignin or lignin containing material.

26 Claims, 7 Drawing Sheets

I

II

III

XVI

XVII

XVIII

XIX

XLI

XLII

XLIII

XLIV

XLV

ENHANCEMENT OF LACCASE REACTIONS

TECHNICAL FIELD

This invention relates to activation of enzymes. More specifically, the invention relates to agents capable of enhancing the activity of laccases and related enzymes.

The invention also relates to methods of oxidizing a substrate in the presence of a laccase enzyme, and an enhancing agent. More specifically, the invention relates to a method of bleaching of dye in solutions, to a method of inhibiting the transfer of a textile dye from a dyed fabric to another fabric when said fabrics are washed together in a wash liquor, to a method of bleaching lignin-containing material, in particular bleaching of pulp for paper production, to a method of treatment of waste water from pulp manufacturing, and to a method of enzymatic polymerization and/or modification of lignin or lignin containing material.

BACKGROUND ART

Laccases (E.C. 1.10.3.2) are enzymes that catalyse the oxidation of a substrate (an electron or hydrogen donor) with oxygen. Such enzymes are known from microbial, plant and animal origins, e.g. from fungi. They are typically copper proteins, i.e. they contain a copper atom or atoms as a prosthetic group.

Use of laccases has been suggested e.g. in bleaching of pulp for paper production, in treatment of waste water from pulp production, for improved bleaching in laundry detergents, for dye transfer inhibition during laundering, and for lignin modification, e.g. in particle board production.

The compound 2,2'-azino-bis (3-ethylbenzothiazoline-6-sulfonate), ABTS, supplied by Boehringer Mannheim, is a chromogenic substrate, and a common peroxidase and phenol oxidase assay agent. These enzymes catalyse the oxidation of ABTS by hydrogen peroxide and dioxygen, respectively, producing a greenish-blue colour, which process may be monitored photometrically.

ABTS has been found to form a stable radical cation when oxidized by a laccase enzyme (polyphenol oxidase, EC 1.10.3.2), and has been proposed to act as a redox mediator for oxidation of non-phenolic lignin model compounds [Bourbonnais R. Paice M G; FEBS Lett (1990) 267 99–102].

Studies on demethylation and delignification of kraft pulp by a laccase enzyme in the presence of ABTS showed that the extent of partial demethylation by laccase was increased in the presence of ABTS [Bourbonnais. R. and Paice, M. G; Appl. Microbiol. Biotechnol. (1992) 36 823–827].

Certain oxidizable substrates e.g. metal ions and phenolic compounds such as 7-hydroxycoumarin (7HCm), vanillin (VAN), and p-hydroxybenzenesulfonate (PHBS), have been described as accelerators or enhancers, able to enhance bleaching reactions (cf. e.g. WO 92/18683, WO 92/18687, and Kato M and Shimizu S. Plant Cell Physiol. 1985 26 (7), pp. 1291–1301 (cf. Table 1 in particular), or Saunders B C. et al., Peroxidase, London, 1964, p. 141 ff).

SUMMARY OF THE INVENTION

It has now surprisingly been found that organic chemical compounds consisting of at least two aromatic rings, of which aromatic rings at least one ring is substituted with one or more of the following atoms: nitrogen, oxygen, and sulfur, and which aromatic rings may furthermore be fused rings, are capable of enhancing the activity of laccase enzymes.

Accordingly, in its first aspect, the invention provides an agent for enhancing the activity of laccase enzymes, which agent is an organic chemical compound consisting of at least two aromatic rings, of which aromatic rings at least one ring is substituted with one or more of the following atoms: nitrogen, oxygen, and sulfur; and which aromatic rings may furthermore be fused rings.

In a more specific aspect, the invention provides an agent for enhancing the activity of laccase enzymes, which agent is an organic chemical compound of the general formula I:

in which general formula A represents a single bond, or one of the following groups: $(-CR^{11}=CR^{15}-)_n$, $(-CR^{11}=N-N=CR^{15}-)$, $(-NR^{11}-)$, $(-CR^{12}=N-)_n$, $(-NR^{11}-CR^{12}=N-N=CR^{15}-)$, $(-NR^{11}-CR^{12}=N-)_n$, $(-CR^{12}=N-NR^{11}-)$, $(-NR^{11}-CR^{12}=CR^{13}-)$ $(-N=N-)$, in which groups n represents an integer of from 1 to 6; or A represents carbon, carbonyl, nitrogen, sulfur, oxygen, selenium, or phosphor, which carbon, phosphor and nitrogen may be unsubstituted or substituted with a substituent group $R^{11}$;

and in which general formula the substituent groups $R^1$–$R^{13}$ and $R^{15}$, which may be identical or different, independently represents any of the following radicals: hydrogen, hydroxy, formyl, carboxy and esters and salts hereof, carbamoyl, sulfo and esters and salts hereof, sulfamoyl, phospho, phosphono, phosphonooxy, sulfandiyl, nitro, amino, phenyl, $C_1$–$C_{14}$-alkyl, $C_1$–$C_5$-alkoxy, carbonyl-$C_1$–$C_5$-alkyl, aryl-$C_1$–$C_5$-alkyl; which carbamoyl, sulfamoyl, and amino groups may furthermore be unsubstituted or substituted once or twice with a substituent group $R^{14}$; and which phenyl may furthermore be unsubstituted or substituted with one or more substituent groups $R^{14}$; and which $C_1$–$C_{14}$-alkyl, $C_1$–$C_5$-alkoxy, carbonyl-$C_1$–$C_5$-alkyl, and aryl-$C_1$–$C_5$-alkyl groups may be saturated or unsaturated, branched or unbranched, and may furthermore be unsubstituted or substituted with one or more substituent groups $R^{14}$;

which substituent group $R^{14}$ represents any of the following radicals: hydroxy, formyl, carboxy and esters and salts hereof, carbamoyl, sulfo and esters and salts hereof, sulfamoyl, nitro, amino, phenyl, aminoalkyl, piperidino, piperazinyl, pyrrolidino, $C_1$–$C_5$-alkyl, $C_1$–$C_5$-alkoxy; which carbamoyl, sulfamoyl, and amino groups may furthermore be unsubstituted or substituted once or twice with hydroxy, $C_1$–$C_5$-alkyl, $C_1$–$C_5$-alkoxy; and which phenyl may furthermore be substituted with one or more of the following radicals: hydroxy, amino, formyl, carboxy and esters and salts hereof, carbamoyl, sulfo and esters and salts hereof, and sulfamoyl; and which $C_1$–$C_5$-alkyl, and $C_1$–$C_5$-alkoxy groups may furthermore be saturated or unsaturated, branched or unbranched, and may furthermore be substituted once or twice with any of the following radicals: hydroxy, amino, formyl, carboxy and esters and salts hereof, carbamoyl, sulfo and esters and salts hereof, and sulfamoyl;

or in which general formula $R^5$ and $R^6$ may together form a group —B—, in which B represents a single bond, the group (—CH=CH—)$_n$, or the group (—CH=N—)$_n$, in which groups n represents an integer of from 1 to 6; or B represents carbon, nitrogen, sulfur, oxygen, selenium, or tellurium, which carbon and nitrogen may be unsubstituted or substituted with a substituent group $R^{14}$ as defined above;

or in which general formula two of the substituent groups $R^1$-$R^{10}$ may together form a group —C—, in which C represents any of the following groups: (—CHR$^{11}$—N=N—), (—CH=CH—)$_n$, (—CH=N—)$_n$, in which groups n represents an integer of from 2 to 4, and in which groups $R^{11}$ is a substituent group as defined above;

or in which general formula $R^5$ and $R^{12}$, and/or $R^6$ and $R^{13}$, when n in the above formula being 1, may together form a group —D—, in which D represents the groups: (—CHR$^{11}$—), (—NR$^{11}$—), (—CR$^{11}$=CR$^{15}$—), (—CR$^{11}$=N—), (—N=CR$^{11}$—), (—O—), (>C=O) or (—S—), and in which groups $R^{11}$ and $R^{15}$ are substituent groups as defined above.

In another specific aspect, the invention provides an agent for enhancing the activity of a laccase enzyme, which agent is an organic chemical compound of the general formula II:

in which the substituent groups $R^1$-$R^8$, which may be identical or different, independently represents any of the following radicals: hydrogen, hydroxy, formyl, carboxy and esters and salts hereof, carbamoyl, sulfo and esters and salts hereof, sulfamoyl, nitro, amino, phenyl, $C_1$-$C_{14}$-alkyl, $C_1$-$C_5$-alkoxy, carbonyl-$C_1$-$C_5$-alkyl, aryl-$C_1$-$C_5$-alkyl; which carbamoyl, sulfamoyl, and amino groups may furthermore be unsubstituted or substituted once or twice with a substituent group $R^9$; and which phenyl may furthermore be unsubstituted or substituted with one or more substituent groups $R^9$; and which $C_1$-$C_{14}$-alkyl, $C_1$-$C_5$-alkoxy, carbonyl-$C_1$-$C_5$-alkyl, and aryl-$C_1$-$C_5$-alkyl groups may be saturated or unsaturated, branched or unbranched, and may furthermore be unsubstituted or substituted with one or more substituent groups $R^9$;

which substituent group $R^9$ represents any of the following radicals: hydroxy, formyl, carboxy and esters and salts hereof, carbamoyl, sulfo and esters and salts hereof, sulfamoyl, nitro, amino, phenyl, $C_1$-$C_5$-alkyl, $C_1$-$C_5$-alkoxy; which carbamoyl, sulfamoyl, and amino groups may furthermore be unsubstituted or substituted once or twice with hydroxy, $C_1$-$C_3$-alkyl, $C_1$-$C_3$-alkoxy; and which phenyl may furthermore be substituted with one or more of the following radicals: hydroxy, amino, formyl, carboxy and esters and salts hereof, carbamoyl, sulfo and esters and salts hereof, and sulfamoyl; and which $C_1$-$C_5$-alkyl, and $C_1$-$C_5$-alkoxy groups may furthermore be saturated or unsaturated, branched or unbranched, and may furthermore be substituted once or twice with any of the following radicals: hydroxy, amino, formyl, carboxy and esters and salts hereof, carbamoyl, sulfo and esters and salts hereof, and sulfamoyl;

or in which general formula two of the substituent groups $R^1$-$R^8$ may together form a group —B—, in which B represents any of the following groups: (—N=N—), (—CH=CH—)$_n$, (—CH=N—)$_n$, (—N=CR$^9$—NR$^{10}$—) or (—N=N—CR$^9$—), in which groups n represents an integer of from 1 to 3, $R^9$ is a substituent group as defined above and $R^{10}$ is defined as $R^9$.

In another aspect, the invention provides a method for oxidizing a substrate with a laccase or a laccase related enzyme, in the presence of oxygen and in the presence of an enhancing agent of the invention.

In a more specific aspect, the invention provides a method for bleaching dye in solutions by treatment with a laccase or a laccase related enzyme in the presence of oxygen in the presence of an enhancing agent of the invention.

In another specific aspect, the invention provides a method of inhibiting the transfer of a textile dye from a dyed fabric to another fabric when said fabrics are washed together in a wash liquor, the method comprising treatment of the wash liquor with a laccase or a laccase related enzyme in the presence of oxygen and in the presence of an enhancing agent of the invention.

In another aspect, the invention provides a method of bleaching lignin-containing material, in particular bleaching of pulp for paper production, the method comprising treatment of the lignin or lignin containing material with a laccase or a laccase related enzyme in the presence of a source of oxygen and in the presence of an enhancing agent of the invention.

In a further aspect, the invention provides a method of enzymatic polymerization and/or modification of lignin or lignin containing material, the method comprising treatment of the lignin or lignin containing material with a laccase or a laccase related enzyme in the presence of a source of oxygen and in the presence of an enhancing agent of the invention.

In a yet further aspect, the invention provides a method of treatment of waste water, in particular waste water from pharmaceutical or chemical industry, e.g. waste water from dye manufacturing, from textile industry, or from pulp manufacturing, the method comprising treatment of the waste water with a laccase or a laccase related enzyme in the presence of a source of oxygen and in the presence of an enhancing agent of the invention.

In a particular aspect, the invention provides a detergent additive capable of inhibiting the transfer of a textile dye from a dyed fabric to another fabric when said fabrics are washed together in a wash liquor, the detergent additive comprising an enzyme exhibiting laccase activity and oxygen and an enhancing agent of the invention.

In other aspects, the invention provides detergent additives and detergent compositions capable of inhibiting the transfer of a textile dye from a dyed fabric to another fabric when said fabrics are washed together in a wash liquor, the detergent composition comprising an enzyme exhibiting laccase activity and oxygen and an enhancing agent of the invention.

BRIEF DESCRIPTION OF DRAWINGS

The present invention is further illustrated by reference to the accompanying drawings, in which:

FIG. 1 shows the specific formulas of some enhancing agents of the invention (I) 6-hydroxy-2-naphtoic acid; (II) 7-methoxy-2-naphtol; (III) 7-amino-2-naphthalene sulfonic acid; (IV) 5-amino-2-naphthalene sulfonic acid; (V) 1,5-diaminonaphthalene; (VI) 7-hydroxy-1,2-naphthimidazole; (VII) 10-methylphenothiazine; (VIII) 10-phenothiazinepropionic acid; (IX) N-hydroxysuccinimide-10-phenothiazine-propionate; (X) benzidine; (XI) 3,3'-dimethylbenzidine; (XII) 3,3'-dimethoxybenzidine; (XIII) 3,3',5,5'-tetramethylbenzidine; (XIV) 4'-hydroxy-4-biphenylcarboxylic acid; (XV) 4-amino-4'-methoxystilbene; (XVI) 4,4'-diaminostilbene-2,2'-disulfonic acid; (XVII) 4,4'-diaminodiphenylamine; (XVIII) 2,7-diaminofluorene; (XIX) 4,4'-dihydroxy-biphenylene; (XX) triphenylamine; (XXI) 10-ethyl-4-phenothiazinecarboxylic acid; (XXII) 10-ethylphenothiazine; (XXIII) 10-propylphenothiazine; (XXIV) 10-isopropylphenothiazine; (XXV) methyl-10-phenothiazinepropionate; (XXVI) 10-phenylphenothiazine; (XXVII) 10-allylphenothiazine; (XXVIII) 10-phenoxazinepropionic acid; (XXIX) 10-(3-(4-methyl-1-piperazinyl)propyl)phenothiazine; (XXX) 10-(2-pyrrolidinoethyl)phenothiazine; (XXXI) 10-methylphenoxazine; (XXXII) iminostilbene; (XXXIII) 2-(p-aminophenyl)-6-methylbenzothiazole-7-sulfonic acid; (XXXIV) N-benzylidene-4-biphenylamine; (XXXV) 5-amino-2-naphthalenesulfonic acid; (XXXVI) 7-methoxy-2-naphtol; (XXXVII) 4,4'-dihydroxybenzophenone; (XXXVIII) N-(4-(dimethylamino)benzylidene)-p-anisidine; (XXXIX) 3-methyl-2-benzothiazolinone(4-(dimethylamino)benzylidene)hydrazone; (XL) 2-acethyl-10-methylphenothiazine; (XLI) 10-(2-hydroxyethyl)phenothiazine; (XLII) 10-(2-hydroxyethyl)phenoxazine; (XLIII) 10-(3-hydroxypropyl)phenothiazine; (XLIV) 4,4'-dimethoxy-N-methyl-diphenylamine; (XLV) vanillin azine.

DETAILED DISCLOSURE OF THE INVENTION

The Enhancing Agent

The present invention relates to the use of chemical compounds for enhancing the activity of laccase enzymes. Accordingly, the invention provides an agent capable of enhancing the effect of a laccase enzyme in the following termed enhancing agent.

The enhancing agent of the invention is an organic chemical compound consisting of at least two aromatic rings, of which aromatic rings at least one ring is substituted with one or more nitrogen, oxygen, and/or sulfur atoms, and which aromatic rings may furthermore be fused rings.

In a more preferred embodiment, the enhancing agent of the invention is an organic chemical compound of the general formula I:

in which general formula A represents a single bond, or one of the following groups: (—CR$^{11}$=CR$^{15}$—)$_n$, (—CR$^{11}$=N—N=CR$^{15}$—), (—NR$^{11}$—), (—CR$^{12}$=N—)$_n$, (—NR$^{11}$—CR$^{12}$=N—N=CR$^{15}$—), (—NR$^{11}$—CR$^{12}$=N—)$_n$, (—CR$^{12}$=N—NR$^{11}$—), (—NR$^{11}$—CR$^{12}$=CR$^{13}$—), (—N=N—), in which groups n represents an integer of from 1 to 6; or A represents carbon, carbonyl, nitrogen, sulfur, oxygen, selenium, or phosphor, which carbon, phosphor and nitrogen may be unsubstituted or substituted with a substituent group R$^{11}$;

and in which general formula the substituent groups R$^1$—R$^{13}$ and R$^{15}$, which may be identical or different, independently represents any of the following radicals: hydrogen, hydroxy, formyl, carboxy and esters and salts hereof, carbamoyl, sulfo and esters and salts hereof, sulfamoyl, phospho, phosphono, phosphonooxy, sulfandiyl, nitro, amino, phenyl, C$_1$–C$_{14}$-alkyl, C$_1$–C$_5$-alkoxy, carbonyl-C$_1$–C$_5$-alkyl, aryl-C$_1$–C$_5$-alkyl; which carbamoyl, sulfamoyl, and amino groups may furthermore be unsubstituted or substituted once or twice with a substituent group R$^{14}$; and which phenyl may furthermore be unsubstituted or substituted with one or more substituent groups R$^{14}$; and which C$_1$–C$_4$-alkyl, C$_1$–C$_5$-alkoxy, carbonyl-C$_1$–C$_5$-alkyl, and aryl-C$_1$–C$_5$-alkyl groups may be saturated or unsaturated, branched or unbranched, and may furthermore be unsubstituted or substituted with one or more substituent groups R$^{14}$;

which substituent group R$^{14}$ represents any of the following radicals: hydroxy, formyl, carboxy and esters and salts hereof, carbamoyl, sulfo and esters and salts hereof, sulfamoyl, nitro, amino, phenyl, aminoalkyl, piperidino, lo piperazinyl, pyrrolidino, C$_1$–C$_5$-alkyl, C$_1$–C$_5$-alkoxy; which carbamoyl, sulfamoyl, and amino groups may furthermore be unsubstituted or substituted once or twice with hydroxy, C$_1$–C$_5$-alkyl, C$_1$–C$_5$-alkoxy; and which phenyl may furthermore be substituted with one or more of the following radicals: hydroxy, amino, formyl, carboxy and esters and salts hereof, carbamoyl, sulfo and esters and salts hereof, and sulfamoyl; and which C$_1$–C$_5$-alkyl, and C$_1$–C$_5$-alkoxy groups may furthermore be saturated or unsaturated, branched or unbranched, and may furthermore be substituted once or twice with any of the following radicals: hydroxy, amino, formyl, carboxy and esters and salts hereof, carbamoyl, sulfo and esters and salts hereof, and sulfamoyl;

or in which general formula R$^5$ and R$^6$ may together form a group —B—, in which B represents a single bond, the group (—CH=CH—)$_n$, or the group (—CH=N—)$_n$, in which groups n represents an integer of from 1 to 6; or B represents carbon, nitrogen, sulfur, oxygen, selenium, or tellurium, which carbon and nitrogen may be unsubstituted or substituted with a substituent group R$^{14}$ as defined above;

or in which general formula two of the substituent groups R$^1$–R$^{10}$ may together form a group —C—, in which C represents any of the following groups: (—CHR$^{11}$—N=N—), (—CH=CH—)$_n$, (—CH=N—)$_n$, in which groups n represents an integer of from 2 to 4, and in which groups R$^{11}$ is a substituent group as defined above;

or in which general formula R$^5$ and R$^{12}$, and/or R$^6$ and R$^{13}$, when n in the above formula being 1, may together form a group —D—, in which D represents the groups: (—CHR$^{11}$—), (—NR$^{11}$—), (—CR$^{11}$=CR$^{15}$—), (—CR$^{11}$=N—), (—N=CR$^{11}$—), (—O—), (>C=O) or (—S—), and in which groups R$^{11}$ and R$^{15}$ are substituent groups as defined above.

In particular embodiments, the enhancing agent is 2-(p-aminophenyl)-6-methylbenzothiazole-7-sulfonic acid, N-(4-(dimethylamino)benzylidene)-p-anisidine, 3-methyl-2-benzothiazolinone(4-(dimethylamino)benzylidene) hydrazone, vanillin azine.

In another preferred embodiment, the enhancing agent of the invention is an organic chemical compound of the general formula II:

in which the substituent groups $R^1$–$R^8$, which may be identical or different, independently represents any of the following radicals: hydrogen, hydroxy, formyl, carboxy and esters and salts hereof, carbamoyl, sulfo and esters and salts hereof, sulfamoyl, nitro, amino, phenyl, $C_1$–$C_{14}$-alkyl, $C_1$–$C_5$-alkoxy, carbonyl-$C_1$–$C_5$-alkyl, aryl-$C_1$–$C_5$-alkyl; which carbamoyl, sulfamoyl, and amino groups may furthermore be unsubstituted or substituted once or twice with a substituent group $R^9$; and which phenyl may furthermore be unsubstituted or substituted with one or more substituent groups $R^9$; and which $C_1$–$C_{14}$-alkyl, $C_1$–$C_5$-alkoxy, carbonyl-$C_1$–$C_5$-alkyl, and aryl-$C_1$–$C_5$-alkyl groups may be saturated or unsaturated, branched or unbranched, and may furthermore be unsubstituted or substituted with one or more substituent groups $R^9$;

which substituent group $R^9$ represents any of the following radicals: hydroxy, formyl, carboxy and esters and salts hereof, carbamoyl, sulfo and esters and salts hereof, sulfamoyl, nitro, amino, phenyl, $C_1$–$C_5$-alkyl, $C_1$–$C_5$-alkoxy; which carbamoyl, sulfamoyl, and amino groups may furthermore be unsubstituted or substituted once or twice with hydroxy, $C_1$–$C_3$-alkyl, $C_1$–$C_3$-alkoxy; and which phenyl may furthermore be substituted with one or more of the following radicals: hydroxy, amino, formyl, carboxy and esters and salts hereof, carbamoyl, sulfo and esters and salts hereof, and sulfamoyl; and which $C_1$–$C_5$-alkyl, and $C_1$–$C_5$-alkoxy groups may furthermore be saturated or unsaturated, branched or unbranched, and may furthermore be substituted once or twice with any of the following radicals: hydroxy, amino, formyl, carboxy and esters and salts hereof, carbamoyl, sulfo and esters and salts hereof, and sulfamoyl;

or in which general formula two of the substituent groups $R^1$–$R^8$ may together form a group —B—, in which B represents any of the following groups: (—N═N—), (—CH═CH—)$_n$, (—CH═N—)$_n$, (—N═CR$^9$—NR$^{10}$—) or (—N═N—CR$^9$—), in which groups n represents an integer of from 1 to 3, $R^9$ is a substituent group as defined above and $R^{10}$ is defined as $R^9$.

In a more specific embodiment, the enhancing agent of the invention is an organic chemical compound of the following formula:

in which formula E represents a single bond, a carbonyl group or one of the following groups: (—CH═CH—)$_n$, (—CH═N—)$_n$ or (—NR$^{11}$—), in which n represents an integer from 1 to 2. The substituents groups $R^1$–$R^{11}$ may be identical or different, independently being one of the following radicals: hydrogen, hydroxy, formyl, carboxy and esters and salts hereof, carbamoyl, sulfo and esters and salts hereof, sulfamoyl, nitro, amino, phenyl, $C_1$–$C_{14}$-alkyl, $C_1$–$C_5$-alkoxy, carbonyl-$C_1$–$C_5$-alkyl, aryl-$C_1$–$C_5$-alkyl; which carbamoyl, sulfamoyl, and amino groups may furthermore be unsubstituted or substituted once or twice with a substituent group $R^{14}$; and which phenyl may furthermore be unsubstituted or substituted with one or more substituent groups $R^{14}$; and which $C_1$–$C_{14}$-alkyl, $C_1$–$C_5$-alkoxy, carbonyl-$C_1$–$C_5$-alkyl, and aryl-$C_1$–$C_5$-alkyl groups may be saturated or unsaturated, branched or unbranched, and may furthermore be unsubstituted or substituted with one or more substituent groups $R^{14}$;

which substituent group $R^{14}$ represents any of the following radicals: hydroxy, formyl, carboxy and esters and salts hereof, carbamoyl, sulfo and esters and salts hereof, sulfamoyl, nitro, amino, phenyl, $C_1$–$C_5$-alkyl, $C_1$–$C_5$-alkoxy; which carbamoyl, sulfamoyl, and amino groups may furthermore be unsubstituted or substituted once or twice with hydroxy, $C_1$–$C_3$-alkyl, $C_1$–$C_3$-alkoxy; and which phenyl may furthermore be substituted with one or more of the following radicals: hydroxy, amino, formyl, carboxy and esters and salts hereof, carbamoyl, sulfo and esters and salts hereof, and sulfamoyl; and which $C_1$–$C_5$-alkyl, and $C_1$–$C_5$-alkoxy groups may furthermore be saturated or unsaturated, branched or unbranched, and may furthermore be substituted once or twice with any of the following radicals: hydroxy, amino, formyl, carboxy and esters and salts hereof, carbamoyl, sulfo and esters and salts hereof, and sulfamoyl;

or in which specific formula two of the substituent groups $R^5$ and $R^6$ may together form a group —B—, in which B represents the groups: (—CH═N—)$_n$, (—CH═CH—) or (—CHR$^{14}$—) in which groups n represents an integer of from 1 to 2 and $R^{14}$ is a substituent group as defined above.

In particular embodiments, the enhancing agent is 4-amino-4'-methoxystilbene, 4,4'-diaminostilbene-2,2'-disulfonic acid, iminostilbene, 4,4'-dihydroxybenzophenone, N-benzylidene-4-biphenylamine, 4,4'-diaminodiphenylamine, 4,4'-dimethoxy-N-methyldiphenylamine, 2,7-diaminofluorene, triphenylamine.

In another specific embodiment, the enhancing agent may be described by the following formula:

in which formula X represents one of the following groups: (—O—), (—S—), (—NR$^{15}$—), (—CHR$^{15}$—), (>C═O), (—CH═CH—), (—CH═N—) and the substituent groups $R^1$–$R^9$ and $R^{15}$, which may be identical or different, independently represents any of the following radicals: hydrogen, hydroxy, formyl, carboxy and 15esters and salts hereof, carbamoyl, sulfo and esters and salts hereof, sulfamoyl, nitro, amino, phenyl, $C_1$–$C_{14}$-alkyl, $C_1$–$C_5$-alkoxy, carbonyl-$C_1$–$C_5$-alkyl, aryl-$C_1$–$C_5$-alkyl; which carbamoyl, sulfamoyl, and amino groups may furthermore be unsubstituted or substituted once or twice with a substituent group $R^{10}$;

and which phenyl may furthermore be unsubstituted or substituted with one or more substituent groups $R^{10}$; and which $C_1-C_{14}$-alkyl, $C_1-C_5$-alkoxy, carbonyl-$C_1-C_5$-alkyl, and aryl-$C_1-C_5$-alkyl groups may be saturated or unsaturated, branched or unbranched, and may furthermore be unsubstituted or substituted with one or more substituent groups $R^{10}$;

which substituent group $R^{10}$ represents any of the following radicals: hydroxy, formyl, carboxy and esters and salts hereof, carbamoyl, sulfo and esters and salts hereof, sulfamoyl, nitro, amino, phenyl, aminoalkyl, piperidino, piperazinyl, pyrrolidino, $C_1-C_5$-alkyl, $C_1-C_5$-alkoxy; which carbamoyl, sulfamoyl, and amino groups may furthermore be unsubstituted or substituted once or twice with hydroxy, $C_1-C_5$-alkyl, $C_1-C_5$-alkoxy; and which phenyl may furthermore be substituted with one or more of the following radicals: hydroxy, amino, formyl, carboxy and esters and salts hereof, carbamoyl, sulfo and esters and salts hereof, and sulfamoyl; and which $C_1-C_5$-alkyl, and $C_1-C_5$-alkoxy groups may furthermore be saturated or unsaturated, branched or unbranched, and may furthermore be substituted once or twice with any of the following radicals: hydroxy, amino, formyl, carboxy and esters and salts hereof, carbamoyl, sulfo and esters and salts hereof, and sulfamoyl;

or in which general formula two of the substituent groups $R^1-R^8$ may together form a group —B—, in which B represents any of the following the groups: (—$CHR^{10}$—N=N—), (—CH=CH—)$_n$, (—CH=N—)$_n$ or (—N=$CR^{10}$—$NR^{11}$—), in which groups n represents an integer of from 1 to 3, $R^{10}$ is a substituent group as defined above and $R^{11}$ is defined as $R^{10}$.

In particular embodiments, the enhancing agent is 10-methylphenothiazine, 10-phenothiazine-propionic acid, N-hydroxysuccinimide-10-phenothiazine-propionate or 10-ethyl-4-phenothiazine-carboxylic acid, 10-ethylphenothiazine, 10-propylphenothiazine, 10-isopropylphenothiazine, methyl-10-phenothiazinepropionate, 10-phenylphenothiazine, 10-allylphenothiazine, 10-(3-(4-methyl-1-piperazinyl)propyl)phenothiazine, 10-(2-pyrrolidinoethyl)phenothiazine, 2-acetyl-10-methyl-phenothiazine, 4-carboxy-10-phenothiazine, 10-methylphenoxazine, 10-ethylphenoxazine, 10-phenoxazine-propionic acid, 4-carboxy-10-phenoxazine-propionic acid, 10-(2-hydroxyethyl)phenothiazine, 10-(2-hydroxyethyl)phenoxazine or 10-(3-hydroxypropyl)phenothiazine.

In another specific embodiment, enhancing agent is a biphenyl derivative of the following formula:

in which the substituent groups $R^1-R^{10}$, which may be identical or different, independently represents any of the following radicals: hydrogen, hydroxy, formyl, carboxy and esters and salts hereof, carbamoyl, sulfo and esters and salts hereof, sulfamoyl, nitro, amino, phenyl, $C_1-C_{14}$-alkyl, $C_1-C_5$-alkoxy, carbonyl-$C_1-C_5$-alkyl, aryl-$C_1-C_5$-alkyl; which carbamoyl, sulfamoyl, and amino groups may furthermore be unsubstituted or substituted once or twice with a substituent group $R^{11}$; and which phenyl may furthermore be unsubstituted or substituted with one or more substituent groups $R^{11}$; and which $C_1-C_{14}$-alkyl, $C_1-C_5$-alkoxy, carbonyl-$C_1-C_5$-alkyl, and aryl-$C_1-C_5$-alkyl groups may be saturated or unsaturated, branched or unbranched, and may furthermore be unsubstituted or substituted with one or more substituent groups $R^{11}$;

which substituent group $R^{11}$ represents any of the following radicals: hydroxy, formyl, carboxy and esters and salts hereof, carbamoyl, sulfo and esters and salts hereof, sulfamoyl, nitro, amino, phenyl, $C_1-C_5$-alkyl, $C_1-C_5$-alkoxy; which carbamoyl, sulfamoyl, and amino groups may furthermore be unsubstituted or substituted once or twice with hydroxy, $C_1-C_3$-alkyl, $C_1-C_3$-alkoxy; and which phenyl may furthermore be substituted with one or more of the following radicals: hydroxy, amino, formyl, carboxy and esters and salts hereof, carbamoyl, sulfo and esters and salts hereof, and sulfamoyl; and which $C_1-C_5$-alkyl, and $C_1-C_5$-alkoxy groups may furthermore be saturated or unsaturated, branched or unbranched, and may furthermore be substituted once or twice with any of the following radicals: hydroxy, amino, formyl, carboxy and esters and salts hereof, carbamoyl, sulfo and esters and salts hereof, and sulfamoyl.

In particular embodiments, the enhancing agent is benzidine, 3,3'-dimethylbenzidine, 3,3'-dimethoxybenzidine, 3,3',5,5'-tetramethylbenzidine, 4'-hydroxy-4-biphenylcarboxylic acid, or 4,4'-dihydroxybiphenylene.

In another specific embodiment, the enhancing agent is a naphthalene derivative of the following formula:

in which the substituent groups $R^1-R^8$, which may be identical or different, independently represents any of the following radicals: hydrogen, hydroxy, formyl, carboxy and esters and salts hereof, carbamoyl, sulfo and esters and salts hereof, sulfamoyl, nitro, amino, phenyl, $C_1-C_{14}$-alkyl, $C_1-C_5$-alkoxy, carbonyl-$C_1-C_5$-alkyl, aryl-$C_1-C_5$-alkyl; which carbamoyl, sulfamoyl, and amino groups may furthermore be unsubstituted or substituted once or twice with a substituent group $R^9$; and which phenyl may furthermore be unsubstituted or substituted with one or more substituent groups $R^9$; and which $C_1-C_{14}$-alkyl, $C_1-C_5$-alkoxy, carbonyl-$C_1-C_5$-alkyl, and aryl-$C_1-C_5$-alkyl groups may be saturated or unsaturated, branched or unbranched, and may furthermore be unsubstituted or substituted with one or more substituent groups $R^9$;

which substituent group $R^9$ represents any of the following radicals: hydroxy, formyl, carboxy and esters and salts hereof, carbamoyl, sulfo and esters and salts hereof, sulfamoyl, nitro, amino, phenyl, $C_1-C_5$-alkyl, $C_1-C_5$-alkoxy; which carbamoyl, sulfamoyl, and amino groups may furthermore be unsubstituted or substituted once or twice with hydroxy, $C_1-C_3$-alkyl, $C_1-C_3$-alkoxy; and which phenyl may furthermore be substituted with one or more of the following radicals: hydroxy, amino, formyl, carboxy and esters and salts hereof, carbamoyl, sulfo and esters and salts hereof, and sulfamoyl; and which $C_1$-$C_5$-alkyl, and $C_1$-$C_5$-alkoxy groups may furthermore be saturated or unsaturated, branched or unbranched, and may furthermore be substituted once or twice with any of the following radicals: hydroxy, amino, formyl, carboxy and esters and salts hereof, carbamoyl, sulfo and esters and salts hereof, and sulfamoyl;

or in which general formula two of the substituent groups $R^1$-$R^8$ may together form a group —B—, in which B represents any of the following groups: (—N=N—), (—CH=CH—)$_n$, (—CH=N—)$_n$, (—N=CR$^9$—NR$^{10}$—) or (—N=N—CR$^9$—), in which groups n represents an integer of from 1 to 3, $R^9$ is a substituent group as defined above and $R^{10}$ is defined as $R^9$.

In particular embodiments, the enhancing agent is 6-hydroxy-2-naphtoic acid, 7-methoxy-2-naphtol, 7-amino-2-naphthalene sulfonic acid, 5-amino-2-naphthalene sulfonic acid, 1,5-diaminonaphthalene, 7-hydroxy-1,2-naphthimidazole, 5-amino-2-naphthalenesulfonic acid, or 7-methoxy-2-naphtol.

The enhancing agent of the invention may be in free form or in the form of an addition salt.

Methods of Oxidizing a Substrate

In another aspect, the invention provides a method of oxidizing a substrate with a laccase enzyme and in the presence of an enhancing agent.

The enhancing agent may be present in free form or in the form of an addition salt.

The enhancing agent may be present in concentrations of from 0.01 to 500 µM, more preferred 0.1 to 250 µM, most preferred 0.5 to 100 µM.

Molecular oxygen from the atmosphere will usually be present in sufficient quantity.

Laccase and Related Enzymes

The enhancing agents of the invention are agents capable of enhancing the activity of laccases and laccase related enzymes. In the context of this invention, laccases and laccase related enzymes contemplate any laccase enzyme comprised by the enzyme classification EC 1.10.3.2, any chatechol oxidase enzyme comprised by the enzyme classification EC 1.10.3.1, any bilirubin oxidase enzyme comprised by the enzyme classification EC 1.3.3.5 or any monophenol monooxygenase enzyme comprised by the enzyme classification EC 1.14.99.1.

Preferably, the laccase employed in the method of the invention is derived from a fungi such as Trametes, e.g. *T. villosa* or *T. versicolor*, Collybia, Fomes, Lentinus, Pleurotus, Rhizoctonia, e.g. *R. solani*, Asperaillus, Neurospora, Podospora, Phlebia, e.g. *P. radiata* (WO 92/01046), Coriolus, e.g. *C. hirsitus* (JP 2-238885), Myceliophthora, e.g. *M. thermophila* or Botrytis. Bilirubin oxidase may preferably be derived from Myrothecium, e.g. *M. verrucaria*.

The laccase or the laccase related enzyme may furthermore be one which is producible by a method comprising cultivating a host cell transformed with a recombinant DNA vector which carries a DNA sequence encoding said laccase as well as DNA sequences encoding functions permitting the expression of the DNA sequence encoding the laccase, in a culture medium under conditions permitting the expression of the laccase enzyme, and recovering the laccase from the culture.

Determination of Laccase Activity (LACU)

Laccase activity is determined from the oxidation of syringaldazin under aerobic conditions. The violet colour produced is photometered at 530 nm. The analytical conditions are 19 µM syringaldazin, 23.2 mM acetate buffer, pH 5.5, 30° C., 1 min. reaction time.

1 laccase unit (LACU) is the amount of enzyme that catalyses the conversion of 1.0 gmole syringaldazin per minute at these conditions.

Determination of Bilirubin Oxidase Activity (Sioma Units)

1 bilirubin oxidase Sigma unit is the amount of enzyme that will oxidize 1.0 µmole of bilirubin per minute at pH 8.4 and 30° C.

Industrial Applications

In a preferred embodiment, the method of the invention finds application for bleaching of dye in solutions.

In another embodiment, the method of the invention finds application for dye transfer inhibition, e.g. for treatment of dyed textiles (cf. e.g. WO 92/18687) or during laundering (cf. e.g. WO 91/05839).

Accordingly, in a specific embodiment, the invention provides a method for inhibiting the transfer of a textile dye from a dyed fabric to another fabric when said fabrics are washed together in a wash liquor, the method comprising treatment of the wash liquor with a laccase or a laccase related enzyme in the presence of an enhancing agent. The textile dye may be a synthetic dye such as an azo dye, or a natural or nature-identical dye.

In a third embodiment, the method of the invention finds application in bleaching of pulp for paper production.

Accordingly, the invention provides a method for bleaching of lignin-containing material, in particular bleaching of pulp for paper production, which method comprises treatment of the lignin or lignin containing material with a laccase or a laccase related enzyme in the presence of an enhancing agent of the invention.

In a fourth embodiment, the method of the invention finds application for lignin modification, e.g. in the manufacture of wood composites, e.g. wood fibre materials such as chipboards, fibre boards, or particle boards, or in the manufacture of laminated wood products, such as laminated beams and plywood.

Accordingly, the invention provides a method for enzymatic polymerization and/or modification of lignin or lignin containing material, which method comprises treatment of the lignin or lignin containing material with a laccase or a laccase related enzyme in the presence of an enhancing agent of the invention.

In a fifth embodiment, the method of the invention finds application in treatment of waste water e.g. waste water from the chemical or pharmaceutical industry, from dye manufacturing, from dye-works, from the textile industry, or from pulp production (cf. e.g. U.S. Pat. No. 4,623,465, or JP-A-2-31887).

In a more specific aspect, the invention provides a method for treatment of waste water from dye manufacturing, from dye-works, from textile industry, or from pulp manufacturing, the method comprising treatment of the waste water with a laccase or a laccase related enzyme in the presence of an enhancing agent of the invention.

Detergent Compositions

According to the invention, the enhancing agent may be added as a component of a detergent composition. As such, it may be included in the detergent composition in the form of a detergent additive. The detergent composition as well as the detergent additive may additionally comprise one or more other enzymes conventionally used in detergents, such as proteases, lipases, amylases, cutinases, cellulases and peroxidases.

In a specific aspect, the invention provides a detergent additive. The enzymes may be included in a detergent composition by adding separate additives containing one or more enzymes, or by adding a combined additive comprising all of these enzymes. A detergent additive of the invention, i.e. a separated additive or a combined additive, can be formulated e.g. as granulates, liquids, slurries, etc. Preferred detergent additive formulations are granulates, in particular non-dusting granulates, liquids, in particular stabilized liquids, slurries, or protected enzymes.

Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition of the invention may be in any convenient form, e.g. as powder, granules, paste or liquid. A liquid detergent may be aqueous, typically containing up to 70% water and 0–30% organic solvent, or nonaqueous.

The detergent composition comprises one or more surfactants, each of which may be anionic, nonionic, cationic, or zwitterionic. The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid or soap. It may also contain 0–40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes, such as amylases, lipases, cutinases, proteases, cellulases and peroxidases.

The detergent may contain 1–65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may comprise one or more polymers. Examples are carboxymethylcellulose (CMC), poly (vinylpyrrolidone) (PVP), polyethyleneglycol (PEG), poly (vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzenesulfonate (NOBS). Alternatively, the bleaching system may comprise peroxyacids of e.g. the amide, imide, or sulfone type.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative as e.g. an aromatic borate ester, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, or perfume.

The pH (measured in aqueous solution at use concentration) will usually be neutral or alkaline, e.g. 7–11.

Particular forms of detergent compositions within the scope of the invention include:

1) A detergent composition formulated as a granulate having a bulk density of at least 600 g/l comprising

| | |
|---|---|
| linear alkylbenzenesulfonate (calculated as acid) | 7–12% |
| alcohol ethoxysulfate (e.g. $C_{12-18}$ alcohol, 1–2 EO) or alkyl sulfate (e.g. $C_{16-18}$) | 1–4% |
| alcohol ethoxylate (e.g. $C_{14-15}$ alcohol, 7 EO) | 5–9% |
| sodium carbonate (as $Na_2CO_3$) | 14–20% |
| soluble silicate (as $Na_2O,SiO_2$) | 2–6% |
| zeolite (as $NaAlSiO_4$) | 15–22% |
| sodium sulfate (as $Na_2SO_4$) | 0–6% |
| sodium citrate/citric acid (as $C_6H_5Na_3O_7/C_6H_8O_7$) | 0–15% |
| sodium perborate (as $NaBO_3.H_2O$) | 11–18% |
| TAED | 2–6% |
| carboxymethylcellulose | 0–2% |
| polymers (e.g. maleic/acrylic acid copolymer, PVP, PEG) | 0–3% |
| enzymes | 0–5% |
| minor ingredients (e.g. suds suppressors, perfume, optical brightener, photobleach) | 0–5% |

2) A detergent composition formulated as a granulate having a bulk density of at least 600 g/l comprising

| | |
|---|---|
| linear alkylbenzenesulfonate (calculated as acid) | 6–11% |
| alcohol ethoxysulfate (e.g. $C_{12-18}$ alcohol, or alkyl sulfate (e.g. $C_{16-18}$) | 1–3% |
| alcohol ethoxylate (e.g. $C_{14-15}$ alcohol, 7 EO) | 5–9% |
| sodium carbonate (as $Na_2CO_3$) | 15–21% |
| soluble silicate (as $Na_2O,2SiO_2$) | 1–4% |
| zeolite (as $NaAlSiO_4$) | 24–34% |
| sodium sulfate (as $Na_2SO_4$) | 4–10% |
| sodium citrate/citric acid (as $C_6H_5Na_3O_7/C_6H_8O_7$) | 0–15% |
| carboxymethylcellulose | 0–2% |

-continued

| | |
|---|---|
| polymers (e.g. maleic/acrylic acid copolymer, PVP, PEG) | 1–6% |
| enzymes | 0–5% |
| minor ingredients (e.g. suds suppressors, perfume) | 0–5% |

3) A detergent composition formulated as a granulate having a bulk density of at least 600 g/l comprising

| | |
|---|---|
| linear alkylbenzenesulfonate (calculated as acid) | 5–9% |
| alcohol ethoxylate (e.g. $C_{12-15}$ alcohol, 7 EO) | 7–14% |
| soap as fatty acid (e.g. $C_{16-22}$) | 1–3% |
| sodium carbonate (as $Na_2CO_3$) | 10–17% |
| soluble silicate (as $Na_2O,2SiO_2$) | 3–9% |
| zeolite (as $NaAlSiO_4$) | 23–33% |
| sodium sulfate (as $Na_2SO_4$) | 0–4% |
| sodium perborate (as $NaBO_3.H_2O$) | 8–16% |
| TAED | 2–8% |
| phosphonate (e.g. EDTMPA) | 0–1% |
| carboxymethylcellulose | 0–2% |
| polymers (e.g. maleic/acrylic acid copolymer, PVP, PEG) | 1–3% |
| enzymes | 0–5% |
| minor ingredients (e.g. suds suppressors, perfume, optical brightener) | 0–5% |

4) A detergent composition formulated as a granulate having a bulk density of at least 600 g/l comprising

| | |
|---|---|
| linear alkylbenzenesulfonate (calculated as acid) | 8–12% |
| alcohol ethoxylate (e.g. $C_{12-15}$ alcohol, 7 EO) | 10–25% |
| sodium carbonate (as $Na_2CO_3$) | 14–22% |
| soluble silicate (as $Na_2O,2SiO_2$) | 1–5% |
| zeolite (as $NaAlSiO_4$) | 25–35% |
| sodium sulfate (as $Na_2SO_4$) | 0–10% |
| carboxymethylcellulose | 0–2% |
| polymers (e.g. maleic/acrylic acid copolymer, PVP, PEG) | 1–3% |
| enzymes | 0–5% |
| minor ingredients (e.g. suds suppressors, perfume) | 0–5% |

5) An aqueous liquid detergent composition comprising

| | |
|---|---|
| linear alkylbenzenesulfonate (calculated as acid) | 15–21% |
| alcohol ethoxylate (e.g. $C_{12-15}$ alcohol, 7 EO or $C_{12-15}$ alcohol, 5 EO) | 12–18% |
| soap as fatty acid (e.g. oleic acid) | 3–13% |
| alkenylsuccinic acid ($C_{12-14}$) | 0–13% |
| aminoethanol | 8–18% |
| citric acid | 2–8% |
| phosphonate | 0–3% |
| polymers (e.g. PVP, PEG) | 0–3% |
| borate (as $B_4O_7$) | 0–2% |
| ethanol | 0–3% |
| propylene glycol | 8–14% |
| enzymes | 0–5% |
| minor ingredients (e.g. dispersants, suds suppressors, perfume, optical brightener) | 0–5% |

6) An aqueous structured liquid detergent composition comprising

| | |
|---|---|
| linear alkylbenzenesulfonate (calculated as acid) | 15–21% |
| alcohol ethoxylate (e.g. $C_{12-15}$ alcohol, 7 EO or $C_{12-15}$ alcohol, 5 EO) | 3–9% |
| soap as fatty acid (e.g. oleic acid) | 3–10% |
| zeolite (as $NaAlSiO_4$) | 14–22% |
| potassium citrate | 9–18% |
| borate (as $B_4O_7$) | 0–2% |
| carboxymethylcellulose | 0–2% |
| polymers (e.g. PEG, PVP) | 0–3% |
| anchoring polymers as e.g. lauryl methacrylate/acrylic acid copolymer; molar ratio 25:1; MW 3800 | 0–3% |
| glycerol | 0–5% |
| enzymes | 0–5% |
| minor ingredients (e.g. dispersants, suds suppressors, perfume, optical brighteners) | 0–5% |

7) A detergent composition formulated as a granulate having a bulk density of at least 600 g/l comprising

| | |
|---|---|
| fatty alcohol sulfate | 5–10% |
| ethoxylated fatty acid monoethanolamide | 3–9% |
| soap as fatty acid | 0–3% |
| sodium carbonate (as $Na_2CO_3$) | 5–10% |
| soluble silicate (as $Na_2O, 2SiO_2$) | 1–4% |
| zeolite (as $NaAlSiO_4$) | 20–40% |
| sodium sulfate (as $Na_2SO_4$) | 2–8% |
| sodium perborate (as $NaBO_3.H_2O$) | 12–18% |
| TAED | 2–7% |
| polymers (e.g. maleic/acrylic acid copolymer, PEG) | 1–5% |
| enzymes | 0–5% |
| minor ingredients (e.g. optical brightener, suds suppressors, perfume) | 0–5% |

8) A detergent composition formulated as a granulate comprising

| | |
|---|---|
| linear alkylbenzenesulfonate (calculated as acid) | 8–14% |
| ethoxylated fatty acid monoethanolamide | 5–11% |
| soap as fatty acid | 0–3% |
| sodium carbonate (as $Na_2CO_3$) | 4–10% |
| soluble silicate (as $Na_2O, 2SiO_2$) | 1–4% |
| zeolite (as $NaAlSiO_4$) | 30–50% |
| sodium sulfate (as $Na_2SO_4$) | 3–11% |
| sodium citrate (as $C_6H_5Na_3O_7$) | 5–12% |
| polymers (e.g. PVP, maleic/acrylic acid copolymer, PEG) | 1–5% |
| enzymes | 0–5% |
| minor ingredients (e.g. suds suppressors, perfume) | 0–5% |

9) A detergent composition formulated as a granulate comprising

| | |
|---|---|
| linear alkylbenzenesulfonate (calculated as acid) | 6–12% |
| nonionic surfactant, | 1–4% |
| soap as fatty acid | 2–6% |
| sodium carbonate (as $Na_2CO_3$) | 14–22% |
| zeolite (as $NaAlSiO_4$) | 18–32% |
| sodium sulfate (as $Na_2SO_4$) | 5–20% |
| sodium citrate (as $C_6H_5Na_3O_7$) | 3–8% |
| sodium perborate (as $NaBO_3.H_2O$) | 4–9% |
| bleach activator (e.g. NOBS or TAED) | 1–5% |

-continued

| | |
|---|---|
| carboxymethylcellulose | 0–2% |
| polymers (e.g. polycarboxylate or PEG) | 1–5% |
| enzymes | 0–5% |
| minor ingredients (e.g. optical brightener, perfume) | 0–5% |

10) An aqueous liquid detergent composition comprising

| | |
|---|---|
| linear alkylbenzenesulfonate (calculated as acid) | 15–23% |
| alcohol ethoxysulfate (e.g. $C_{12-15}$ alcohol, 2–3 EO) | 8–15% |
| alcohol ethoxylate (e.g. $C_{12-15}$ alcohol, 7 EO or $C_{12-15}$ alcohol, 5 EO) | 3–9% |
| soap as fatty acid (e.g. lauric acid) | 0–3% |
| aminoethanol | 1–5% |
| sodium citrate | 5–10% |
| hydroptrope (e.g. sodium toluenesulfonate) | 2–6% |
| borate (as $B_4O_7$) | 0–2% |
| carboxymethylcellulose | 0–1% |
| ethanol | 1–3% |
| propylene glycol | 2–5% |
| enzymes | 0–5% |
| minor ingredients (e.g. polymers, dispersants, perfume, optical brighteners) | 0–5% |

11) An aqueous liquid detergent composition comprising

| | |
|---|---|
| linear alkylbenzenesulfonate (calculated as acid) | 20–32% |
| alcohol ethoxylate (e.g. $C_{12-15}$ alcohol, 7 EO or $C_{12-15}$ alcohol, 5 EO) | 6–12% |
| aminoethanol | 2–6% |
| citric acid | 8–14% |
| borate (as $B_4O_7$) | 1–3% |
| polymer (e.g. maleic/acrylic acid copolymer, anchoring polymers as e.g. lauryl methacrylate/acrylic acid copolymer and CMC) | 0–3% |
| glycerol | 3–8% |
| enzymes | 0–5% |
| minor ingredients (e.g. hydrotropes, dispersants, perfume, optical brighteners) | 0–5% |

12) A detergent composition formulated as a granulate having a bulk density of at least 600 g/l comprising

| | |
|---|---|
| anionic surfactant (linear alkylbenzenesulfonate, alkyl sulfate, alpha-olefinsulfonate, alpha-sulfo fatty acid methyl esters, alkanesulfonates, soap) | 25–40% |
| nonionic surfactant (e.g. alcohol ethoxylate) | 1–10% |
| sodium carbonate (as $Na_2CO_3$) | 8–25% |
| soluble silicates (as $Na_2O, 2SiO_2$) | 5–15% |
| sodium sulfate (as $Na_2SO_4$) | 0–5% |
| zeolite (as $NaAlSiO_4$) | 15–28% |
| sodium perborate (as $NaBO_3.4H_2O$) | 0–20% |
| bleach activator (TAED or NOBS) | 0–5% |
| enzymes | 0–5% |
| minor ingredients (e.g. perfume, optical brighteners) | 0–3% |

13) Detergent formulations as described in 1)–12) where the content of linear alkylbenzenesulfonate—or a part of it—is substituted by alkyl sulfate ($C_{12}$–$C_{18}$).

14) Detergent formulations as described in 1)–13) which contain a stabilized or encapsulated peracid either as an additional component or as a substitute for already specified bleach systems.

15) Detergent compositions as described in 3), 7), 9) and 12) where the content of perborate is substituted with percarbonate.

16) Detergent composition formulated as a nonaqueous detergent liquid comprising a liquid nonionic surfactant as e.g. linear alkoxylated primary alcohol, a builder system (e.g. phosphate), enzyme and alkali. The detergent may also comprise anionic surfactant and/or a bleach system.

The following examples further illustrate the present invention, and they are not intended to be in any way limiting to the scope of the invention as claimed.

EXAMPLE 1

Bleaching of Direct Blue 1 with Bilirubin Oxidase and 10-Methylphenothiazine

Figure 1A:
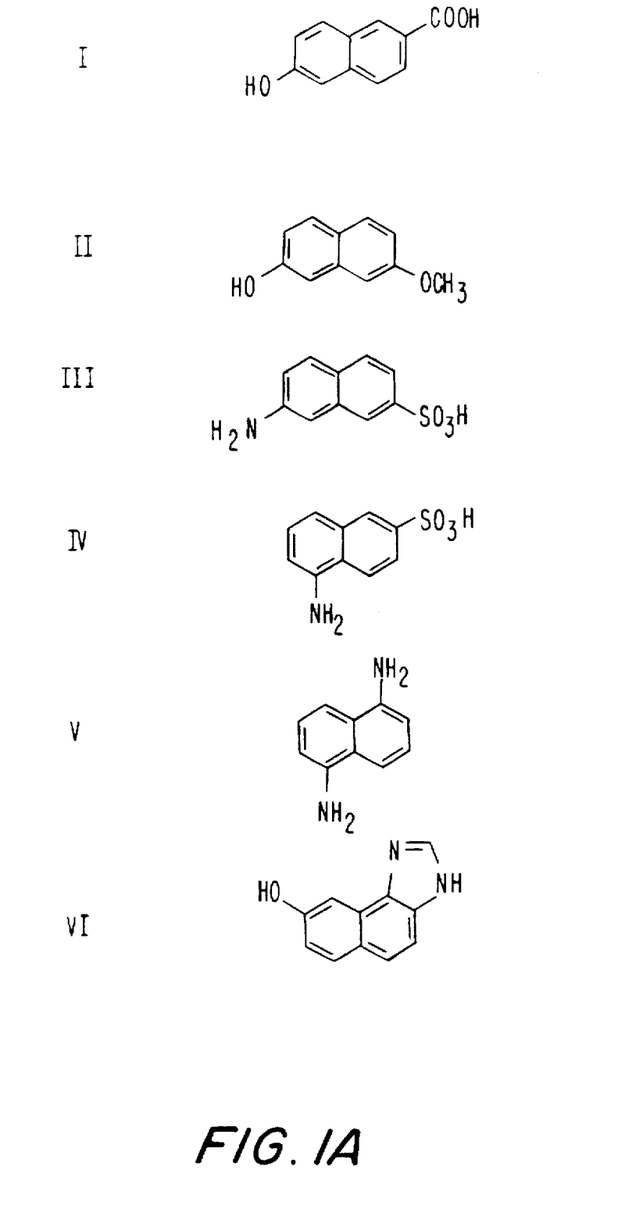
Figure 1B:
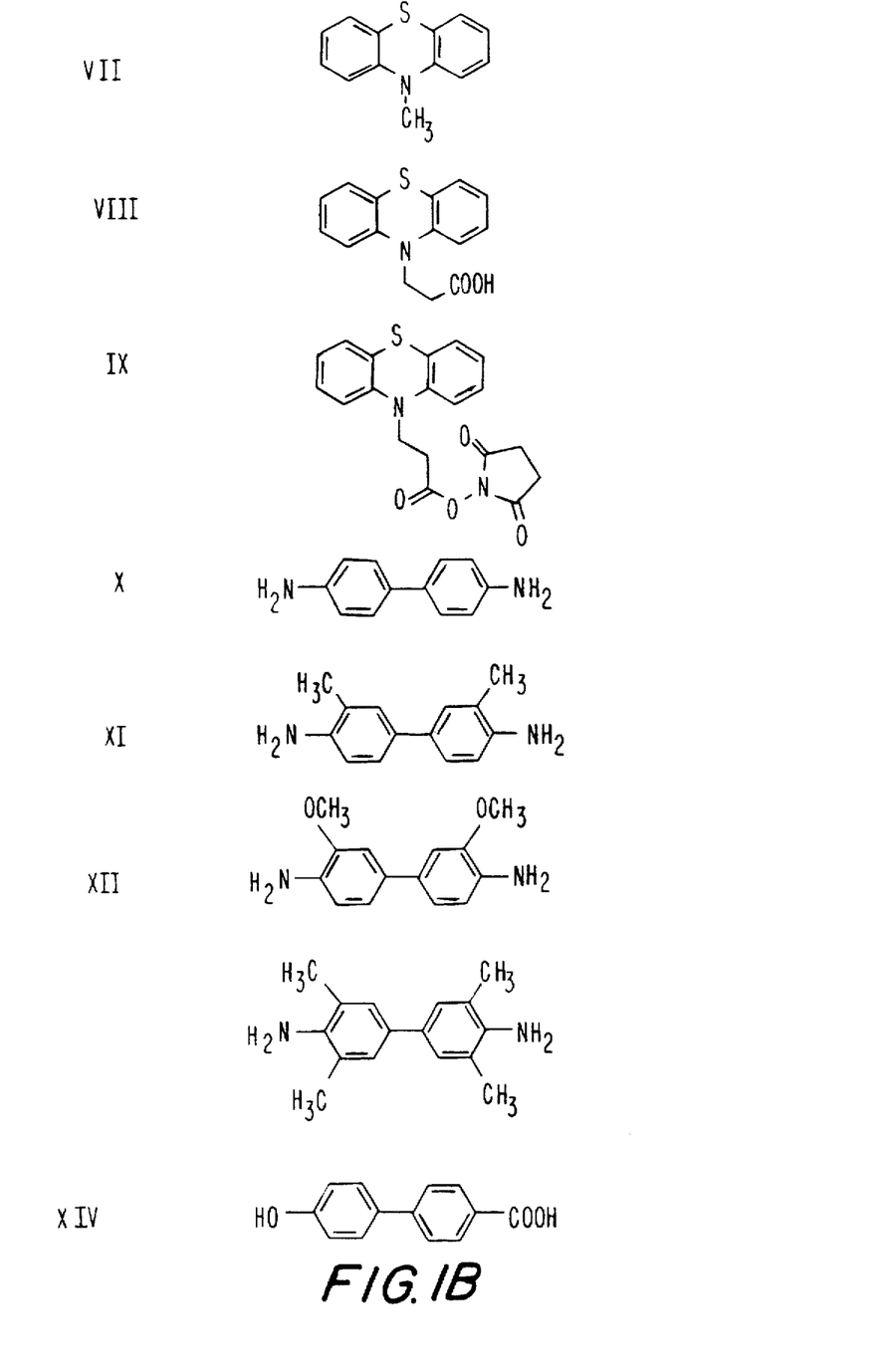
Figure 1C:
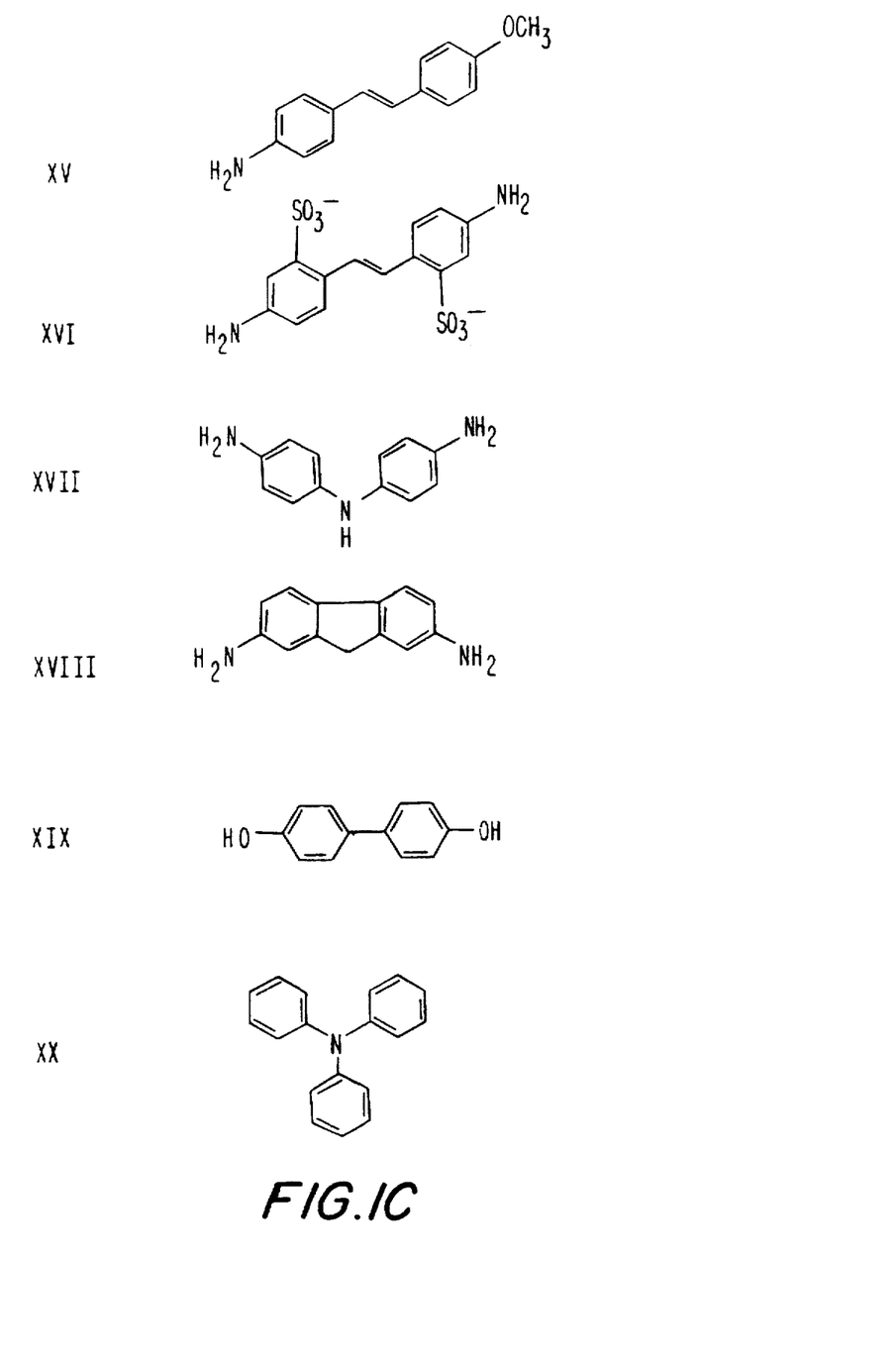
Figure 1D:
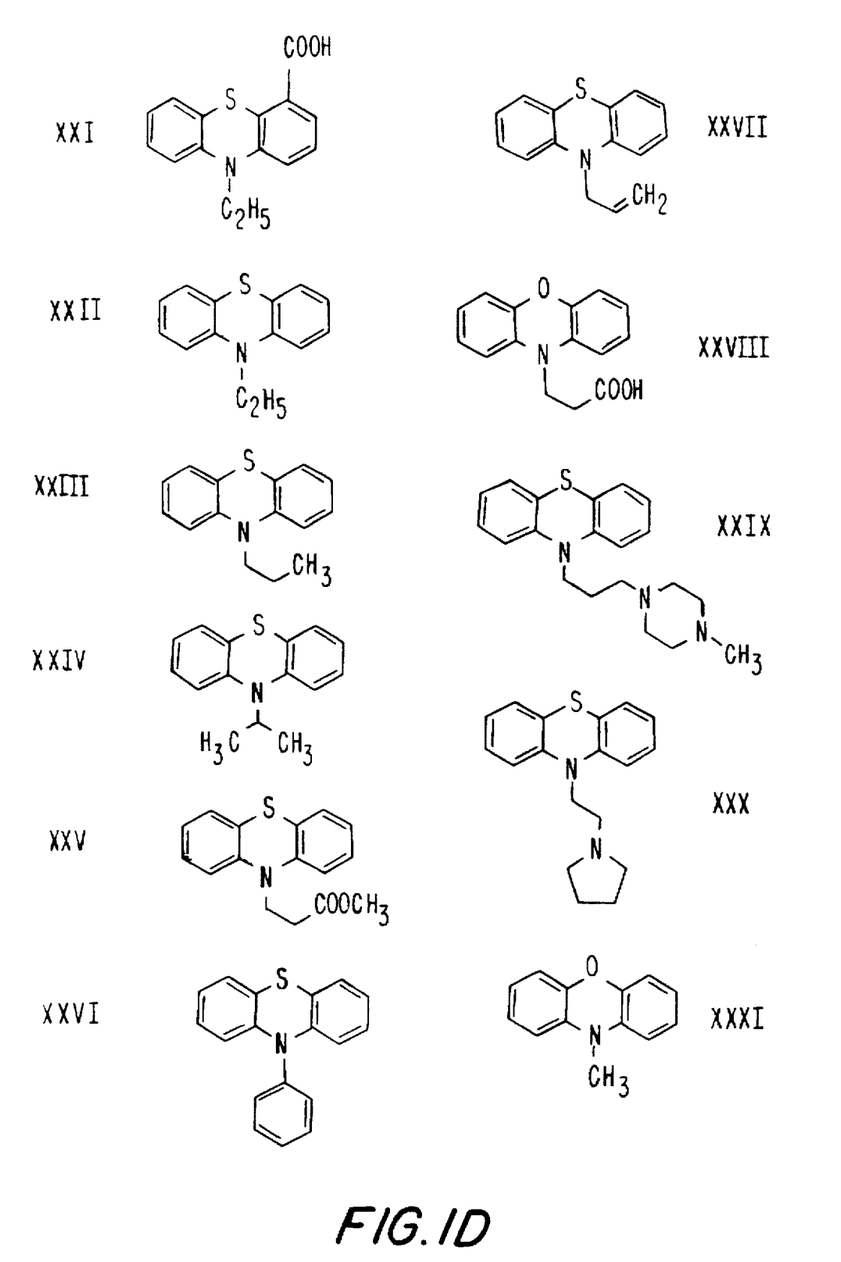
Figure 1E:
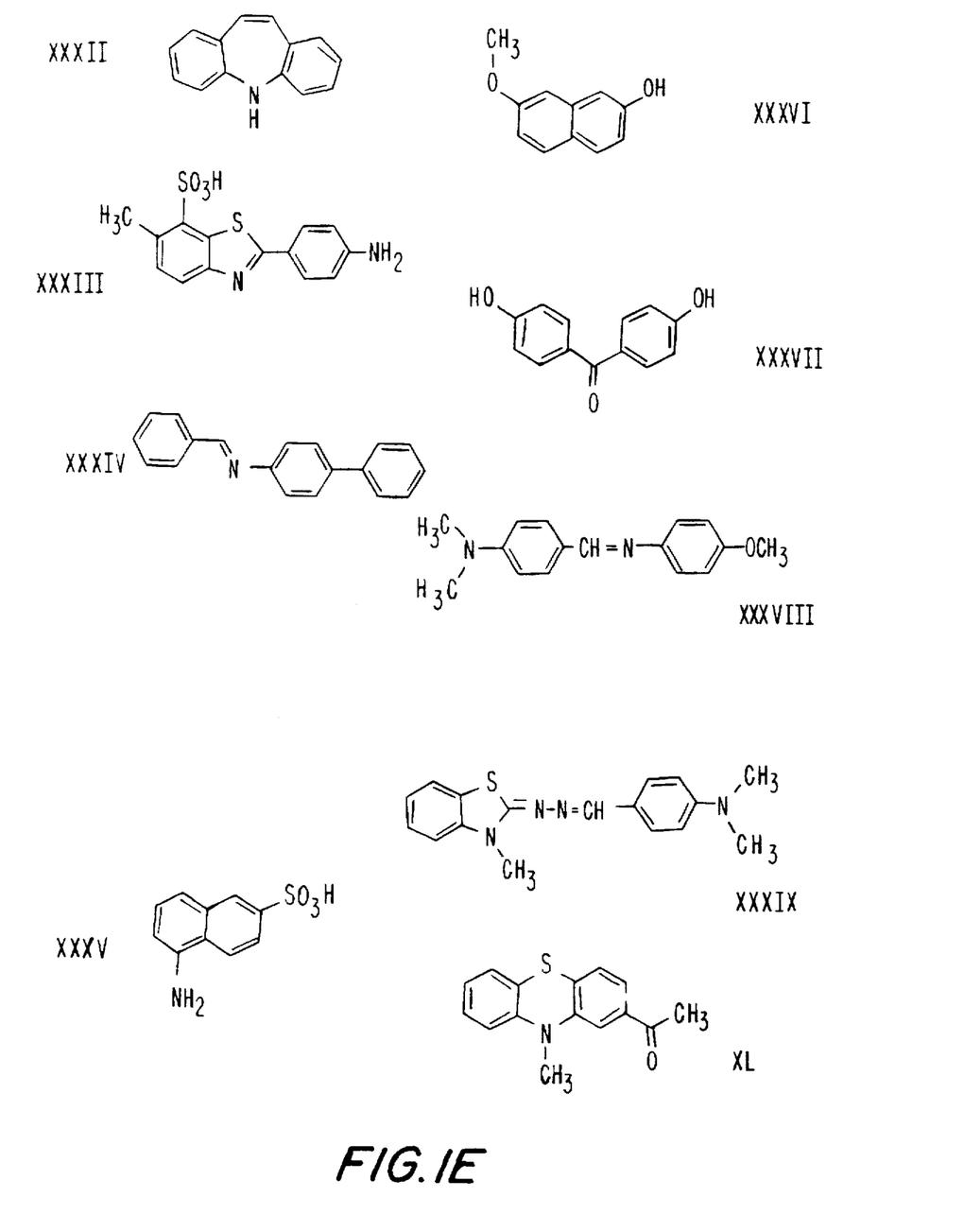
Figure 1F:
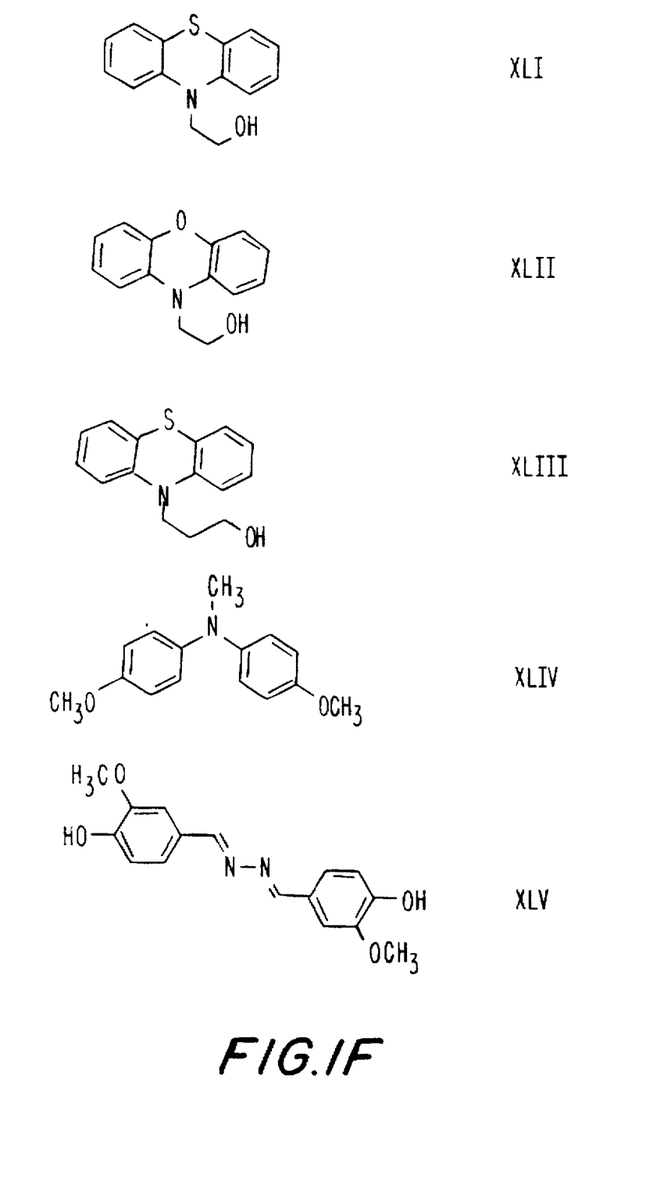
Figure 2:
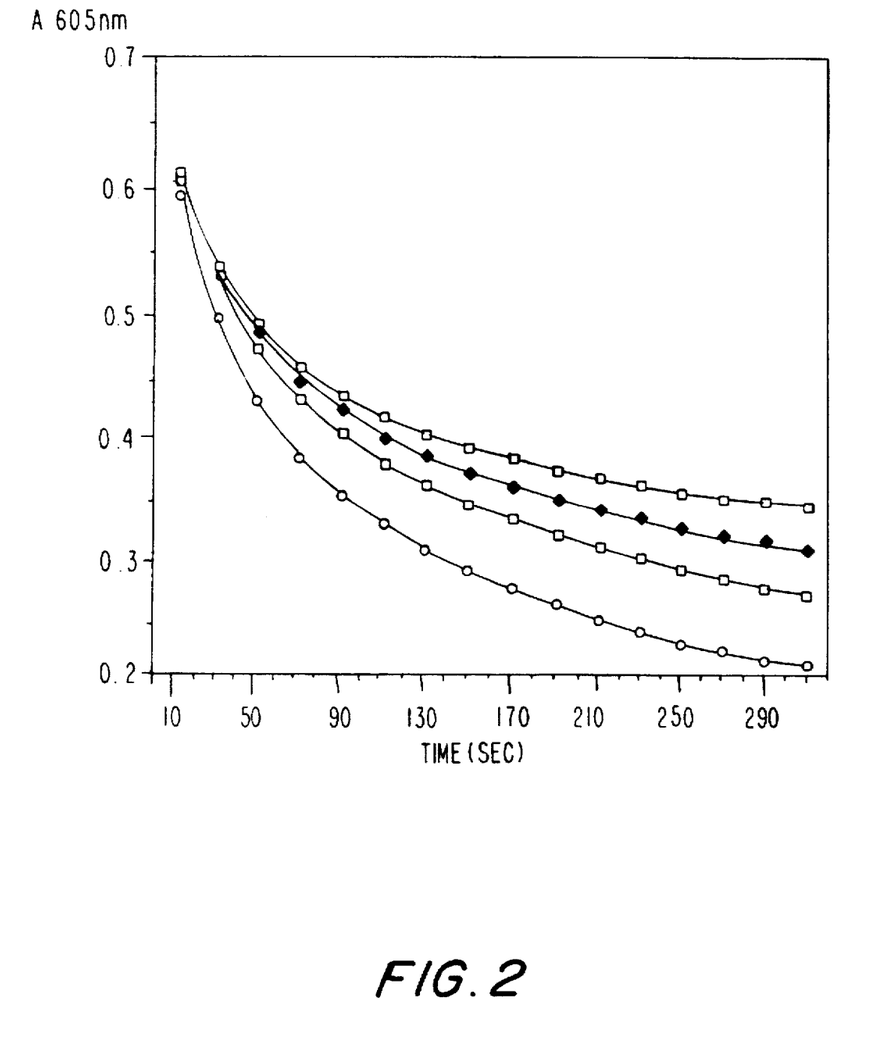
FIG. 2 shows the bleaching of Direct Blue 1 with bilirubin oxidase and 10-methylphenothiazine (MPT) (☐ 0 µM MPT; ♦ 2.5 µM MPT; ■ 5.0 µM MPT; ◊ 10.0 µM MPT).

The bleaching of Direct Blue 1 (DB1) by bilirubin oxidase obtained from Sigma with and without 10-methylphenothiazine (MPT) is presented in the attached FIG. 2.

The following conditions were used:

| | Final concentrations |
|---|---|
| Buffer | 50 mM phosphate, pH 7 |
| MPT | 0, 2.5, 5, or 10 µM |
| DB1 | ≈ $Abs_{605\ nm}$ = 0.6 |
| Bilirubin oxidase | 0.027 Sigma units/ml |

The experiment was started by the addition of enzyme, and the absorbance at 605 nm was monitored for 5 minutes. The temperature was 25° C.

No attempt to maintain a constant concentration of dissolved oxygen was made.

As evidenced by FIG. 2, bleaching is enhanced by increasing concentrations of the enhancer of the invention.

EXAMPLE 2

Bleaching of Direct Blue 1

Bilirubin oxidase: *Myrothecium verrucaria* bilirubin oxidase was purchased from Sigma (B-0390). A stock solution was made containing 27 Sigma units/ml, which was stored in the freezer until use.

Laccase obtained from Trametes villosa: 800 ml culture broth of *Trametes villosa*, CBS 678.70, was filtered with filter aid to give a clear filtrate, which was concentrated and washed by ultrafiltration on a membrane with a cut-off of 6–8 kDa. One ml samples of concentrated preparation was applied onto a Q-Sepharose HP column (Pharmacia, Sweden) equilibrated with 0.1M fosfate pH 7, and the laccase was eluted with a flat NaCl gradient around 0.25M. Fractions with laccase activity from 10 runs were pooled and concentrated by ultrafiltration to an activity of 500 LACU/ml.

Enhancers: Chemicals were obtained from Sigma-Aldrich, Janssen Chimica, Kodak, Tokyo Kasai Organic Chemicals or Daiichi Pure Chemicals Co. N-methylated derivatives of phenothiazine and phenoxazine were made by methylation with methyliodide as described by Cornel Bodea and Ioan Silberg in "Recent Advances in the Chemistry of Phenothiazines" (Advances in heterocyclic chemistry, 1968, Vol. 9, pp. 321–460); B. Cardillo & G. Casnati in Tetrahedron, 1967, Vol. 23, p. 3771. Phenothiazine and phenoxazine propionic acids may be prepared as described in *J. Org. Chem.* 15, 1950, pp. 1125–1130. Hydroxyethyl and hydroxypropyl derivatives of phenothiazine and phenoxazine may be prepared as described by G. Cauquil in *Bulletin de la Society Chemiaue de France*, 1960, p. 1049.

Due to low solubility some of the enhancers were dissolved in a small volume of ethanol before dilution in water.

The following conditions were used:

|  | Final concentration |
|---|---|
| 400 μl 50 mM Britton-Robinson buffer, pH 5.5 and pH 7.0 respectively, | 20 mM |
| 200 μl DB1 ~ 3.0 Abs. Units (610 nm) | 0.6 ($A_{610\ nm}$) |
| 200 μl 50 μM enhancer | 10 μM |
| 200 μl Enzyme |  |

Reagents were mixed in a 1 cm thermostated cuvette at 30° C. and the bleaching was started by addition of enzyme.

The bleaching was detected spectrophotometrically at 610 nm, which is the absorption peak of DB1. After 5 sec. bleaching was followed for 4 minutes.

From the results presented in Table 1–2, below, it appears that adding enhancers of the invention a much faster bleaching of the dye can be obtained compared to the experiment without enhancer. Enzyme dosages given are in the final incubation mixture.

TABLE 1

Bleaching of Direct Blue 1 with *Trametes villosa* laccase, obtained as described above, at pH 5.5 (0.1 LACU/ml) and pH 7.0 (1 LACU/ml).

|  | DB1 bleaching in 4 minutes (−ΔmAbs/4 min) | |
|---|---|---|
| Enhancer | pH 5.5 | pH 7.0 |
| No enhancer | 0 | 0 |
| 10-Phenothiazinepropionic acid | 387 | 182 |
| 10-Methyl-phenothiazine | 222 | 22 |
| 4'-Hydroxy-4-biphenyl-carboxylic acid | 46 | 34 |
| 4,4'-Diaminostilbene-2,2'-disulfonic acid | 3.5 | 6 |
| 6-Hydroxy-2-naphthoic acid | 12 | 20 |
| 10-Methylphenoxazine | 364 | 296 |
| 10-Phenoxazinepropionic acid | 364 | 268 |
| 10-Ethyl-4-phenothiazinepropionic acid | 411 | 175 |
| 10-(2-Hydroxyethyl)-phenothiazine | 373 | 184 |
| 10-(2-Hydroxyethyl)-phenoxazine | 429 | 192 |
| 10-(3-Hydroxypropyl)-phenothiazine | 428 | 219 |
| 4,4'-Dimethoxy-N-methyl-diphenylamine | 210 | 113 |
| Vanillin azine | 118 | 5 |

TABLE 2

Bleaching of Direct Blue 1 with *Myrothecium verrucaria* bilirubin oxidase, obtained as described above, at pH 5.5 (0.00675 Sigma units/ml) and pH 7.0 (0.0675 Sigma units/ml).

|  | DB1 bleaching in 4 minutes (−ΔmAbs/4 min) | |
|---|---|---|
| Enhancer | pH 5.5 | pH 7.0 |
| No enhancer | 68 | 207 |
| 10-Phenothiazinepropionic acid | 95 | 244 |
| 10-Methyl-phenothiazine | 76 | 250 |
| 10-Methylphenoxazine | 143 | 374 |
| 10-Phenoxazinepropionic acid | 96 | 347 |
| 10-Ethyl-4-phenothiazinepropionic acid | 103 | 293 |

We claim:

1. A method of oxidizing a substrate, comprising treating the substrate with an enzyme selected from the group consisting of laccase, chatechol oxidase, monophenol monooxygenase and bilirubin oxidase and an enhancing agent of the following formula:

in which

X is (—O—), (—S—), (—$NR^{15}$—), (—$CHR^{15}$—), (>C=O), (—CH=CH—), (—CH=N—), or (—N=N—); and $R^1$–$R^9$ and $R^{15}$, which may be identical or different, independently are a radical selected from the group consisting of: hydrogen, hydroxy, formyl, carboxy and esters and salts thereof, carbamoyl, sulfo and esters and salts of, sulfamoyl, phospho, phosphono, phosphonooxy and esters and salts thereof, nitro, amino, phenyl, $C_1$–$C_{14}$-alkyl, $C_1$–$C_5$-alkoxy, carbonyl-$C_1$–$C_5$-alkyl, and amyl-$C_1$–$C_5$-alkyl; in which the carbamoyl, sulfamoyl, and amino groups may be unsubstituted or substituted once or twice with a substituent group $R^{10}$; in which phenyl may be unsubstituted or substituted with one or more substituent groups $R^{10}$; and in which $C_1$–$C_{14}$-alkyl, $C_1$–$C_5$-alkoxy, carbonyl-$C_1$–$C_5$-alkyl, and aryl-$C_1$–$C_5$-alkyl groups may be saturated or unsaturated, branched or unbranched, and may be unsubstituted or substituted with one or more substituent groups $R^{10}$; in which $R^{10}$ independently represents a radical selected from the group consisting of hydroxy, formyl, carboxy and esters and salts thereof, carbamoyl, sulfo and esters and salts thereof, sulfamoyl, phospho, phosphono, phosphonooxy and esters and salts thereof, nitro, amino, phenyl, aminoalkyl, piperidino, piperazinyl, pyrrolidino, $C_1$–$C_5$-alkyl, and $C_1$–$C_5$-alkoxy; in which the carbamoyl, sulfamoyl, and amino groups may be unsubstituted or substituted once or twice with hydroxy, $C_1$–$C_5$-alkyl, or $C_1$–$C_5$-alkoxy; in which phenyl may be substituted with one or more radicals selected from the group consisting of hydroxy, amino, formyl, carboxy and esters and salts thereof, carbamoyl, sulfo and esters and salts of, and sulfamoyl; and in which $C_1$–$C_5$-alkyl and $C_1$–$C_5$-alkoxy groups may be saturated or unsaturated, branched or unbranched, and unsubstituted or substituted once or twice with any radicals selected from he group consisting of hydroxy, amino, formyl, carboxy and esters and salts thereof, carbamoyl, sulfo and esters and salts thereof, and sulfamoyl; or in which two of $R^1$–$R^8$ may together form a group —B— which is selected from the group consisting of (—$CHR^{10}$—N=N—), (—CH=CH—), (—CH=N—)$_n$ and (—N=$CR^{10}$—$NR^{11}$—), in which n is an integer of from 1 to 3, $R^{10}$ is a substituent group as defined above and $R^{11}$ is defined as $R^{10}$.

2. The method according to claim 1, in which the enzyme is a laccase.

3. The method according to claim 2, in which X is (—O—) or (—S—) and $R^5$ is an alkyl group which is unsubstituted or is substituted with one or more $R^{10}$ groups.

4. The method according to claim 2, in which the enhancing agent is 10-methylphenothiazine, 10-phenothiazine-propionic acid, N-hydroxysuccinimide-10-phenothiazine-propionate, 10-ethyl-4-phenothiazine-carboxylic acid, 10-ethylphenothiazine, 10-propylphenothiazine, 10-isopropylphenothiazine, methyl-10- phenothiazinepropionate, 10-phenylphenothiazine, 10-allylphenothiazine, 10-(3-(4-methyl-1-piperazinyl) propyl)phenothiazine, 10-(2-pyrrolidinoethyl) phenothiazine, 2-acetyl-10-methylphenothiazine, 4carboxy-1 0-phenothiazine propionic acid, 1 0-methylphenoxazine, 10-ethylphenoxazine, 10-phenoxazine-propionic acid, 4-carboxy-10-phenoxazine-propionic acid, 10-(2-hydroxyethyl)phenothiazine, 10-(2-hydroxyethyl) phenoxazine or 10-(3-hydroxypropyl)phenothiazine.

5. A detergent additive comprising an enzyme exhibit laccase activity and an enhancing agent of the following formula:

in which
X is (—O—), (—S—), (—NR$^{15}$—), (—CHR$^{15}$—), (>C=O), (—CH=CH—), (—CH=N—), or (—N=N—); and R$^1$–R$^9$ and R$^{15}$, which may be identical or different, independently are a radical selected from the group consisting of: hydrogen, hydroxy, formyl, carboxy and esters and salts thereof, carbamoyl, sulfo and esters and salts thereof, sulfamoyl, phospho, phosphono, phosphonooxy, and esters and salts thereof, nitro, amino, phenyl, $C_1$–$C_{14}$-alkyl, $C_1$–$C_5$-alkoxy, carbonyl-$C_1$–$C_5$-alkyl, and aryl-$C_1$–$C_5$-alkyl; in which the carbamoyl, sulfamoyl, and amino groups may be unsubstituted or substituted once or twice wit a substituent group R$^{10}$; in which phenyl may be unsubstituted or substituted with one or more substituent groups R$^{10}$; and in which $C_1$–$C_{14}$-alkyl, $C_1$–$C_5$-alkoxy, carbonyl-$C_1$–$C_5$-alkyl, and aryl-$C_1$–$C_5$-alkyl groups may be saturated or unsaturated, branched or unbranched, and may be unsubstituted or substituted with one or more substituent groups R$^{10}$; in which R$^{10}$ independently represents a radical selected from the group consisting of hydroxy, formyl, carboxy and esters and salts thereof, carbamoyl, sulfo ad esters and salts of, sulfamoyl, phospho, phosphono, phosphonooxy and esters and salts thereof, nitro, amino, phenyl, aminoalkyl, piperidino, piperazinyl, pyrrolidino, $C_1$–$C_5$-alkyl, and $C_1$–$C_5$-alkoxy; in which the carbamoyl, sulfamoyl, and amino groups may be unsubstituted or substituted once or twice with hydroxy, $C_1$–$C_5$-alkyl, or $C_1$–$C_5$-alkoxy; in which phenyl may be substituted with one or more radicals selected from the group consisting of hydroxy, amino, formyl, carboxy and esters and salts thereof, carbamoyl, sulfo and esters and salts thereof, and sulfamoyl; and in which $C_1$–$C_5$-alkyl and $C_1$–$C_5$-alkoxy groups may be sated or unsaturated, branched or unbranched, and unsubstituted or substituted once or twice with any radicals selected from the group consisting of hydroxy, amino, formyl, carboxy and esters and salts thereof, carbamoyl sulfo and esters and salts of, and sulfamoyl; or in which two of R$^1$–R$^8$ may together form a group —B— which is selected from the group consisting of (—CHR$^{10}$—N=N—), (—CH=CH—)$_n$, (—CH=N—)$_n$ and (—N=CR$^{10}$—NR$^{11}$—), in which n is an integer of from 1 to 3, R$^{10}$ is a substituent group as defined above and R$^{11}$ is defined as R$^{10}$.

6. The detergent additive according to claim 5, in which X is (—O—) or (—S—) and R$^5$ is an all group which is unsubstituted or is substituted with one or more R$^{10}$ groups.

7. The detergent additive according to claim 5, in which the enhancing agent is 10-methylphenothiazine.

8. The detergent additive according to claim 5, in which the enhancing agent is 10-phenothiazine-propionic acid.

9. The detergent additive according to claim 5, in which the enhancing agent is N-hydroxysuccinimide 10-phenothiazinepropionate.

10. The detergent additive according to clam 5, in which the enhancing agent is 10-ethyl4-phenothiazine-carboxylic acid.

11. The detergent additive according to claim 5, in which the enhancing agent is 10-ethylphenothiazine.

12. The detergent additive according to claim 5, in which the enhancing agent is 10-propylphenothiazine.

13. The detergent additive according to claim 5, in which the enhancing agent is 10-isopropylphenothiazine.

14. The detergent additive according to claim 5, in which the enhancing agent is methyl-10-phenothiazinepropionate.

15. The detergent additive according to claim 5, in which the enhancing agent is 10-phenylphenothiazine.

16. The detergent additive according to claim 5, in which the enhancing agent is 10-allylphenothiazine.

17. The detergent additive according to claim 5, in which the enhancing agent is 10-(3-(4-methyl-piperazinyl)propyl) phenothiazine.

18. The detergent additive according to claim 5, in which the enhancing agent is 10-(2-pyrrolidinoethyl) phenothiazine.

19. The detergent additive according to claim 5, in which the enhancing agent is 2-acetyl-10-methylphenothiazine.

20. The detergent additive according to claim 5, in which the enhancing agent is 10-methylphenoxazine.

21. The detergent additive according to claim 5, in which the enhancing agent is 10-(2-hydroxyethyl)phenothiazine.

22. The detergent additive according to claim 5, in which the enhancing agent is 10-(2-hydroxyethyl)phenoxazine.

23. The detergent additive according to claim 5, in which the enhancing agent is 10-(3-hydroxypropyl)phenothiazine.

24. A detergent composition comprising a detergent additive according to claim 4 and a surfactant.

25. The detergent composition according to claim 24, in which X is (—O—) or (—S—) and R$^5$ is an alkyl group which is unsubstituted or substituted with one or more R$^{10}$ groups.

26. The detergent composition according to claim 24, in which the enhancing agent is 10-methylphenothiazine, 10-phenothiazine-propionic acid, N-hydroxysuccinimide-10-phenothiazine-propionate, 10-ethyl-4phenothiazine-carboxylic acid, 10-ethylphenothiazine, 10-propylphenothiazine, 10-isopropylphenothiazine, methyl-10-phenothiazinepropionate, 10-phenylphenothiazine, 10-allylphenothiazine, 10-(3-(4-methyl-1-piperazinyl)propyl)phenothiazine, 10-(2-pyrrolidinoethyl)phenothiazine, 2-acetyl-10-methylphenothiazine, 10-methylphenoxazine, 10-(2-hydroxyethyl)phenothiazine, 10-(2-hydroxyethyl) phenoxazine or 10-(3-hydroxypropyl)phenothiazine.

* * * * *